US009364287B2

(12) United States Patent
DeBenedictis et al.

(10) Patent No.: US 9,364,287 B2
(45) Date of Patent: Jun. 14, 2016

(54) METHOD FOR REDUCING PAIN OF DERMATOLOGICAL TREATMENTS

(75) Inventors: Leonard C. DeBenedictis, Palo Alto, CA (US); Joseph L. Dallarosa, Redwood City, CA (US)

(73) Assignee: RELIANT TECHNOLOGIES, INC., Mountain View, CA (US)

( * ) Notice: Subject to any disclaimer, the term of this patent is extended or adjusted under 35 U.S.C. 154(b) by 2450 days.

(21) Appl. No.: 12/134,009

(22) Filed: Jun. 5, 2008

(65) Prior Publication Data
US 2008/0306418 A1    Dec. 11, 2008

Related U.S. Application Data

(60) Provisional application No. 60/942,175, filed on Jun. 5, 2007.

(51) Int. Cl.
*A61B 18/20* (2006.01)
*A61H 9/00* (2006.01)
*A61B 18/00* (2006.01)

(52) U.S. Cl.
CPC .............. *A61B 18/203* (2013.01); *A61H 9/005* (2013.01); *A61H 9/0007* (2013.01); *A61H 9/0071* (2013.01); *A61B 2018/00005* (2013.01); *A61B 2018/00452* (2013.01)

(58) Field of Classification Search
CPC .... A61H 9/0007; A61H 9/005; A61H 9/0071
USPC ........ 601/2, 3, 15, 16, 80, 160; 604/289, 310, 604/311; 606/9; 607/107
See application file for complete search history.

(56) References Cited

U.S. PATENT DOCUMENTS

| 3,861,383 A | * | 1/1975 | Kovach ........................ 601/160 |
| 4,014,347 A | | 3/1977 | Halleck et al. |
| 4,595,008 A | * | 6/1986 | Guibert ........................ 607/107 |
| 5,447,530 A | | 9/1995 | Guibert et al. |
| 5,449,378 A | | 9/1995 | Schouenborg |
| 5,580,350 A | * | 12/1996 | Guibert et al. ............... 607/107 |

(Continued)

FOREIGN PATENT DOCUMENTS

| AU | 779100 B2 | 9/2000 |
| CA | 2364098 A1 | 9/2000 |

(Continued)

OTHER PUBLICATIONS

Evans, Jeff. "Match Vein Tx to Patient Preference, Tolerance". Dec. 2005. Skin and Allergy News. pp. 16-17.*

(Continued)

*Primary Examiner* — Valerie L Woodward
(74) *Attorney, Agent, or Firm* — Thompson Hine LLP; Toan Vo

(57) ABSTRACT

A method of reducing the level of pain experienced by a patient during a pain-inducing dermatological treatment by using non-pharmacologic means is described. The method employs the use of multiple bursts of a gas to stimulate a touch sensation in or near the tissue to be treated using the dermatological treatment in order to reduce and/or relieve pain. The method can be used alone or can be used in combination with other non-pharmacologic and/or pharmacologic methods of relieving pain in order to make a patient more comfortable during or following the dermatological treatment.

26 Claims, 2 Drawing Sheets

(56) References Cited

U.S. PATENT DOCUMENTS

| | | | |
|---|---|---|---|
| 5,660,836 A | 8/1997 | Knowlton | |
| 5,727,556 A * | 3/1998 | Weth et al. | 600/439 |
| 5,755,753 A | 5/1998 | Knowlton | |
| 5,871,524 A | 2/1999 | Knowlton | |
| 5,919,219 A | 7/1999 | Knowlton | |
| 5,941,902 A | 8/1999 | Holcomb | |
| 5,948,009 A | 9/1999 | Tu | |
| 5,948,011 A | 9/1999 | Knowlton | |
| 6,011,994 A | 1/2000 | Kronberg | |
| 6,063,079 A | 5/2000 | Hovda et al. | |
| 6,068,596 A * | 5/2000 | Weth et al. | 600/437 |
| 6,086,585 A | 7/2000 | Hovda et al. | |
| 6,091,989 A | 7/2000 | Swerdlow et al. | |
| 6,091,994 A | 7/2000 | Loos | |
| 6,109,268 A | 8/2000 | Thapliyal et al. | |
| 6,139,545 A | 10/2000 | Utley et al. | |
| 6,210,402 B1 | 4/2001 | Olsen et al. | |
| 6,217,534 B1 * | 4/2001 | Natalicio | 601/155 |
| 6,228,078 B1 | 5/2001 | Eggers et al. | |
| 6,254,600 B1 | 7/2001 | Willink et al. | |
| 6,264,652 B1 | 7/2001 | Eggers et al. | |
| 6,277,116 B1 | 8/2001 | Utely et al. | |
| 6,296,638 B1 | 10/2001 | Davison et al. | |
| 6,309,387 B1 | 10/2001 | Eggers et al. | |
| 6,311,090 B1 | 10/2001 | Knowlton | |
| 6,387,380 B1 | 5/2002 | Knowlton | |
| 6,405,090 B1 | 6/2002 | Knowlton | |
| 6,408,212 B1 | 6/2002 | Neev | |
| 6,413,255 B1 | 7/2002 | Stern | |
| 6,432,103 B1 | 8/2002 | Ellsberry et al. | |
| 6,445,955 B1 | 9/2002 | Michelson et al. | |
| 6,453,202 B1 | 9/2002 | Knowlton | |
| 6,461,350 B1 | 10/2002 | Underwood et al. | |
| 6,461,354 B1 | 10/2002 | Olsen et al. | |
| 6,481,104 B1 | 11/2002 | Parker et al. | |
| 6,535,767 B1 | 3/2003 | Kronberg | |
| 6,544,261 B2 | 4/2003 | Ellsberry et al. | |
| 6,572,594 B2 * | 6/2003 | Satterfield et al. | 604/290 |
| 6,659,106 B1 | 12/2003 | Hovda et al. | |
| 6,679,908 B2 | 1/2004 | Shimizu | |
| 6,697,670 B2 | 2/2004 | Chomenky et al. | |
| 6,719,754 B2 | 4/2004 | Underwood et al. | |
| 6,746,447 B2 | 6/2004 | Davison et al. | |
| 6,766,202 B2 | 7/2004 | Underwood et al. | |
| 6,832,996 B2 | 12/2004 | Woloszko et al. | |
| 6,843,789 B2 | 1/2005 | Goble | |
| 6,896,672 B1 | 5/2005 | Eggers et al. | |
| 6,902,554 B2 | 6/2005 | Huttner | |
| 6,920,883 B2 | 7/2005 | Bessette et al. | |
| 6,930,590 B2 | 8/2005 | Ling et al. | |
| 6,949,096 B2 | 9/2005 | Davison et al. | |
| 6,991,631 B2 | 1/2006 | Woloszko et al. | |
| 7,001,381 B2 | 2/2006 | Harano et al. | |
| 7,004,941 B2 | 2/2006 | Tvinnereim et al. | |
| 7,020,528 B2 | 3/2006 | Neev | |
| 7,117,034 B2 | 10/2006 | Kronberg | |
| 7,131,969 B1 | 11/2006 | Hovda et al. | |
| 7,241,293 B2 | 7/2007 | Davison | |
| 7,331,957 B2 | 2/2008 | Woloszko et al. | |
| 7,389,145 B2 | 6/2008 | Kilgore et al. | |
| 7,422,586 B2 | 9/2008 | Morris et al. | |
| 7,452,358 B2 | 11/2008 | Stern et al. | |
| 7,473,251 B2 | 1/2009 | Knowlton et al. | |
| 7,601,149 B2 | 10/2009 | DiCarlo et al. | |
| 7,762,964 B2 | 7/2010 | Slatkine | |
| 7,762,965 B2 | 7/2010 | Slatkine | |
| 7,824,394 B2 | 11/2010 | Manstein | |
| 8,073,550 B1 | 12/2011 | Spertell | |
| 8,216,218 B2 | 7/2012 | Burns et al. | |
| 8,406,894 B2 | 3/2013 | Johnson et al. | |
| 2001/0025176 A1 | 9/2001 | Ellsberry et al. | |
| 2002/0087155 A1 | 7/2002 | Underwood et al. | |
| 2002/0133149 A1 | 9/2002 | Bessette | |
| 2002/0169442 A1 | 11/2002 | Neev | |
| 2002/0193789 A1 | 12/2002 | Underwood et al. | |
| 2003/0117371 A1 | 6/2003 | Roberts et al. | |
| 2003/0208194 A1 | 11/2003 | Hovda et al. | |
| 2003/0212351 A1 | 11/2003 | Hissong et al. | |
| 2003/0212396 A1 | 11/2003 | Eggers et al. | |
| 2003/0225403 A1 | 12/2003 | Woloszko et al. | |
| 2004/0098065 A1 | 5/2004 | Hagglof et al. | |
| 2004/0127895 A1 | 7/2004 | Flock et al. | |
| 2004/0206365 A1 | 10/2004 | Knowlton | |
| 2004/0210214 A1 | 10/2004 | Knowlton | |
| 2005/0055055 A1 | 3/2005 | Neev | |
| 2005/0152905 A1 | 7/2005 | Omoigui | |
| 2005/0217682 A1 | 10/2005 | Orton | |
| 2005/0234439 A1 | 10/2005 | Underwood | |
| 2005/0267454 A1 | 12/2005 | Hissong et al. | |
| 2005/0288665 A1 | 12/2005 | Woloszko | |
| 2006/0004306 A1 | 1/2006 | Altshuler et al. | |
| 2006/0047281 A1 | 3/2006 | Kreindel | |
| 2006/0089688 A1 | 4/2006 | Panescu | |
| 2006/0171890 A1 | 8/2006 | Yeomans et al. | |
| 2006/0212077 A1 | 9/2006 | Pilla et al. | |
| 2006/0217636 A1 | 9/2006 | Braig et al. | |
| 2006/0293722 A1 | 12/2006 | Slatkine et al. | |
| 2007/0010811 A1 | 1/2007 | Stern et al. | |
| 2007/0060921 A1 | 3/2007 | Janssen et al. | |
| 2007/0066971 A1 | 3/2007 | Podhajsky | |
| 2007/0078290 A1 | 4/2007 | Esenaliev | |
| 2007/0093797 A1 | 4/2007 | Chan et al. | |
| 2007/0093798 A1 | 4/2007 | DeBenedictis et al. | |
| 2007/0142863 A1 | 6/2007 | Bradley | |
| 2007/0167943 A1 | 7/2007 | Janssen et al. | |
| 2007/0219604 A1 | 9/2007 | Yaroslavsky et al. | |
| 2007/0219605 A1 | 9/2007 | Yaroslavsky et al. | |
| 2008/0015565 A1 | 1/2008 | Davison | |
| 2008/0015568 A1 | 1/2008 | Paul et al. | |
| 2008/0058784 A1 | 3/2008 | Manstein et al. | |
| 2008/0091179 A1 | 4/2008 | Durkin et al. | |
| 2008/0119828 A1 | 5/2008 | Nelson et al. | |
| 2008/0188779 A1 | 8/2008 | Vallero | |
| 2008/0214968 A1 | 9/2008 | Milne et al. | |
| 2008/0215039 A1 | 9/2008 | Slatkine et al. | |
| 2008/0288035 A1 | 11/2008 | Gill et al. | |
| 2008/0294226 A1 | 11/2008 | Moffitt et al. | |
| 2009/0171424 A1 | 7/2009 | Britva et al. | |
| 2009/0287207 A1 | 11/2009 | Stern et al. | |
| 2010/0145321 A1 | 6/2010 | Altshuler et al. | |
| 2010/0179455 A1 | 7/2010 | Nebrigic et al. | |
| 2010/0179531 A1 | 7/2010 | Nebrigic et al. | |
| 2011/0015687 A1 | 1/2011 | Nebrigic et al. | |
| 2011/0172586 A1 | 7/2011 | Hennings et al. | |
| 2011/0202048 A1 | 8/2011 | Nebrigic | |

FOREIGN PATENT DOCUMENTS

| | | |
|---|---|---|
| EP | 1158919 | 12/2001 |
| EP | 1407720 A1 | 4/2004 |
| JP | 11504828 | 5/1999 |
| JP | 2002537939 A | 11/2002 |
| JP | 2007268297 A | 10/2007 |
| WO | 9634568 A1 | 11/1996 |
| WO | 0053113 | 9/2000 |
| WO | 2008069647 A1 | 6/2008 |

OTHER PUBLICATIONS

Ersek, "Transcutaneous Electrical Neurostimulation: A New Therapeutic Modality for Controlling Pain," Clin. Ortop. Relat. Res., 1977, 128:314-24.

Fletcher, "Painless Depo-Medroxyprogesterone Acetate (DMPA) Injections Using the 'Pinch Technique,'" J. Obstet. Gynaecol., 2004, 24(5):562-3.

International Search Report and Written Opinion, PCT/US08/65983, Oct. 1, 2008, 9 pages.

Saijo et al., "Lack of Pain Reduction by a Vibrating Local Anesthetic Attachment: A Pilot Study," Aneth. Prog., 2005, 52(2):62-4.

U.S. Appl. No. 60/942,175, filed Jun. 5, 2007, Leonard C. DeBenedictis.

USPTO, Office Action issued in related U.S. Appl. No. 12/823,214 dated Jul. 23, 2012.

(56) References Cited

OTHER PUBLICATIONS

Office Action issued in related U.S. Appl. No. 12/649,781 dated Jul. 24, 2012.

Junger, M. et al., "Local therapy and treatment costs of chronic, venous leg ulcers with electrical stimulation (Dermapulse): a prospective, placebo controlled, double blind trial", Wound Rep Reg (2008) 480-487.

Kim YH et al., "Effect of pulsed radiofrequency for postherpetic neuralgia", Acta Anaesthesiol Scand 2008; 52:1140-1143, Singapore.

Van Zundert, J. et al., "Pulsed radiofrequency adjacent to the cervical dorsal root ganglion in chronic cervical radicular pain: a double blind sham controlled randomized clinical trial", Pain 127 (2007) 173-182.

Rosted P. et al., "Use of Stimulation techniques in pain treatment", Ugeskr Laeger. May 15, 2006; 168(20):1982-6 (abstract only of Danish article).

Apkarian, AV et al., "Heat-induced pain diminishes vibrotactile perception: a touch gate", Somatosensory and Motor Research, vol. 11, No. 3, 1994, pp. 259-267.

Pevzner et al., "Pulsed radiofrequency treatment of severe radicular pain", Harefuah. Mar. 2005;144(3):178-80, 231. (article in Hebrew).

Mikeladze et al, "Pulsed radiofrequency application in treatment of chronic zygapophyseal joint paint", The Spine Journal 3 (2003) 360-362.

Fisher GH et al., "Concurrent use of a handheld forced cold air device minimizes pteient discomfort during fractional photothermolysis", Dermatol Surg 2005, 31:1242-1244.

Maeda Y. et al, "Low frequencies, but not high frequencies of bi-polar spinal cord stimulation reduce cutaneous and muscle hyperalgesia induced by nerve injury", Pain 138 (2008) 143-152.

Rottmann S. et al, "Electrical low-frequency stimulation induces homotopic long-term depression of nociception and pain from hand in man", Clinical Neurophysiology 119 (2008) 1895-1904.

Gold, MH, "Treatment of wrinkles and elastosis using vacuum-assisted bipolar radiofrequency heating of the dermis", Dermatol Surg 2007; 33:300-309.

Gildenberg, PL "History of electrical neuromodulation for chronic pain", Pain Medicine, vol. 7, No. S1, 2006.

USPTO, Office Action issued in related U.S. Appl. No. 12/823,214 dated Jan. 31, 2013.

USPTO, Office Action issued in related U.S. Appl. No. 12/823,214 dated Jun. 6, 2013.

USPTO, Notice of Allowance issued in U.S. Appl. No. 12/649,781 dated Apr. 23, 2013.

USPTO, Notice of Allowance issued in U.S. Appl. No. 12/823,544 dated Jun. 9, 2014.

USPTO, Office Action issued in U.S. Appl. No. 13/941,077 dated Jun. 13, 2014.

USPTO, Office Action issued in U.S. Appl. No. 12/823,544 dated Aug. 19, 2013.

USPTO, Notice of Allowance issued in U.S. Appl. No. 13/941,077 dated Aug. 20, 2014.

USPTO, Notice of Allowance issued in U.S. Appl. No. 12/649,909 dated Jul. 23, 2014.

USPTO, Office Action issued in U.S. Appl. No. 12/649,909 dated Sep. 17, 2013.

USPTO, Office Action issued in U.S. Appl. No. 13/941,077 dated Dec. 11, 2013.

USPTO, Office Action issued in U.S. Appl. No. 12/823,544 dated Dec. 5, 2013.

USPTO, final Office Action issued in U.S. Appl. No. 12/823,214 dated Jan. 6, 2014.

* cited by examiner

METHOD FOR REDUCING PAIN OF DERMATOLOGICAL TREATMENTS

CROSS-REFERENCE TO RELATED APPLICATIONS

This application claims the benefit of and priority under 35 U.S.C. §119(e) to U.S. Provisional Patent Application Ser. No. 60/942,175, "Method for Reducing Pain of Dermatological Treatments," filed Jun. 5, 2007, which is incorporated herein by reference in its entirety.

FIELD OF THE INVENTION

This invention relates generally to a method of reducing the level of pain experienced by a patient during a pain-inducing dermatological treatment. More particularly, it relates to a method of reducing the pain experienced by a patient during a dermatological treatment by using multiple bursts of a gas to stimulate a touch sensation in or near the tissue to be treated using the pain-inducing dermatological treatment.

BACKGROUND OF THE INVENTION

A number of methods of providing dermatological treatments, such as, for example, intense pulsed light based treatments and laser treatments, produce significant levels of pain in patients, leading to the use of anesthetics or analgesics to make patients more comfortable during and immediately following these treatment. Systemic analgesics have been used to reduce pain, but these can lead to unwanted side effects and can be less effective than desired. Topical anesthetics are more commonly used but these can also produce unwanted side effects, including systemic uptake of the anesthetic. Also, as only lower concentrations of topical anesthetics are currently marketed in the United States, physicians often use compounded materials containing higher concentrations of anesthetic. The use of compounded materials presents concerns about product stability, homogeneity and quality in addition to concerns about side effects and systemic uptake.

A number of non-pharmacologic methods of reducing pain have been used for different purposes. For example, transcutaneous electroneurostimulation has been shown to relieve chronic and acute pain (Ersek (1977) Transcutaneous electrical neurostimulation: a new therapeutic modality for controlling pain, Clin Ortop Relat Res. 128:314-24). Applying pressure or pinching skin before and during an injection has been widely reported to reduce the severity of the pain of the injection (Fletcher (2004) Painless Depo-medroxyprogesterone acetate (DMPA) injections using the 'pinch technique', J Obstet Gynaecol 24(5):562-3). The use of vibratory stimulation has also been proposed to reduce pain, but results have not been conclusive (Saijo et al. (2005) Lack of pain reduction by a vibrating local anesthetic attachment: a pilot study, Aneth Prog 52(2):62-4). These non-pharmacologic methods require that some sort of physical contact is used to stimulate a response in tissue in order to be effective. However, implementing a method using stimulation based on physical contact with tissue can be problematic when combined with a dermatological treatment which may also require contact with the tissue. For example, the delivery mechanism for the dermatological treatment device can interfere with the stimulation by directly contacting or covering the tissue. If the dermatological treatment device requires the use of a contact plate or window, using the contact plate or window itself to stimulate a response in tissue can be difficult. If the stimulation is based on a touch stimulus, the amount of pressure that needs to be applied to the contact plate or window in order to stimulate the tissue can be more than enough pressure to deform the tissue, which in turn can affect the dermatological treatment. Also, if the stimulation is based on a touch stimulus, it may require that the delivery handpiece is vibrated or is repeatedly put in contact and removed from contact with the tissue while the treatment is delivered, which in turn can affect the dermatological treatment. Further, devices which incorporate a means for stimulating tissue in a delivery handpiece can be substantially more complicated to design, manufacture and maintain.

Thus, a need exists for non-pharmacologic methods of reducing the pain of dermatological treatments by stimulating a touch sensation in a patient which are compatible with the various sorts of dermatological treatment devices on the market and in development. Such non-pharmacologic methods of reducing pain by stimulating a touch sensation can be used alone in order to reduce pain during or immediately following a dermatological treatment, or can be used to supplement other methods of analgesia and/or anesthesia.

SUMMARY OF THE INVENTION

The present invention is directed to a method of reducing the level of pain experienced by a patient during or immediately following a pain-inducing dermatological treatment, comprising: stimulating a touch sensation in a patient in an area in or near a region of tissue to be treated immediately before, during, or immediately following a pain-inducing dermatological treatment, wherein the stimulating a touch sensation is achieved by directing multiple bursts of a gas at or near the region of tissue so as to reduce the level of pain experienced by the patient during or immediately following the dermatological treatment. In another embodiment, the present invention is directed to a method of reducing the dosage of anesthetic required by a patient undergoing a pain-inducing dermatological treatment, comprising: stimulating a touch sensation in a patient in an area in or near a region of tissue to be treated immediately before, during, or immediately following a pain-inducing dermatological treatment, wherein the stimulating a touch sensation is achieved by directing multiple bursts of a gas at or near the region of tissue, and wherein the stimulating reduces the dosage of anesthetic required to reduce the level of pain experienced by a patient undergoing the pain-inducing dermatological treatment.

BRIEF DESCRIPTION OF THE DRAWINGS

The invention has other advantages and features which will be more readily apparent from the following detailed description of the invention an the appended claims, when taken in conjunction with the accompanying drawings, in which:

DETAILED DESCRIPTION

Figure 1:
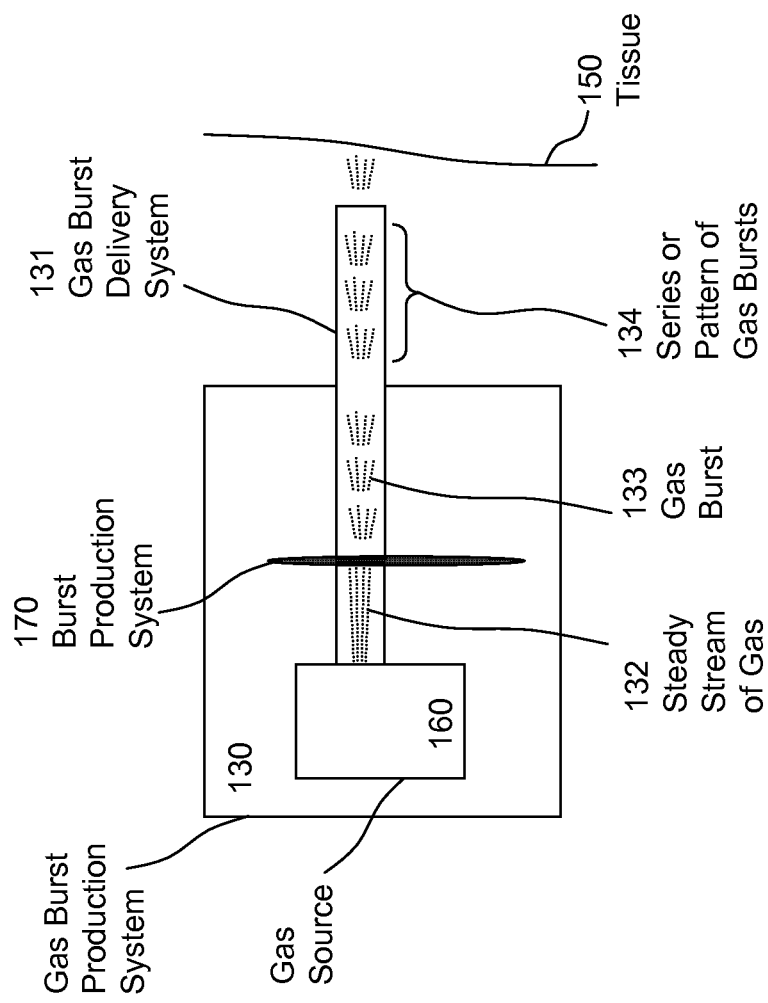
FIG. 1 is a drawing illustrating an example of a gas burst production system being used to deliver a burst of gas to a tissue.

A number of different types of devices are used to deliver dermatological treatments to various types of tissue to achieve various desired medical and/or cosmetic outcomes in the tissue. Under many treatment conditions, these dermatological treatments can produce pain in the patient undergoing the treatment. The devices used to deliver these dermatological treatments can employ one or more forms of electromagnetic radiation, such as, for example, electrical energy, radiofrequency energy, thermal energy, and optical energy, including laser energy, intense pulsed light, etc. In one example, various forms of electromagnetic radiation have been used to treat medical and/or cosmetic conditions such as hypervascular lesions, pigmented lesions, acne scars, rosacea, hypertrichosis, verruca, actinic keratoses, psoriasis, for hair removal, to treat the nail, nail plate or nail matrix, to deliver photodynamic therapy, etc. Additionally, various forms of electromagnetic radiation have also been used for solely cosmetic purposes to achieve a better cosmetic appearance by resurfacing the skin and remodeling the different layers of skin, to improve the appearance of wrinkled or aged skin and/or to tighten skin, and to remove hair. Generally, skin resurfacing is understood to be the process by which the top layers of the skin are completely removed by using chemicals, mechanical abrasion or optical energy to promote the development of new, more youthful looking skin and stimulate the generation and growth of new skin. In laser skin remodeling, laser energy penetrates into at least a portion of the deeper layers of the skin and is aimed at stimulating the generation of and/or altering the structure of extra-cellular matrix materials, such as collagen, that contribute to the youthful appearance of skin.

During dermatological treatments utilizing electromagnetic radiation, the electromagnetic radiation is directed at the skin surface or at the layers of tissue below the surface of the skin of a patient. Generally, optical energy based dermatological treatments operate at one or more wavelengths that are absorbed by one or more of the natural chromophores in the skin, such as, for example, blood, melanin and/or water, although chromophores can also be added to the tissue. In the case when water is used as the primary chromophore, cellular and interstitial water absorbs the optical energy and transforms the optical energy into thermal energy. The transport of thermal energy in tissues during treatment is a complex process involving conduction, convection, radiation, metabolism, evaporation and phase change that vary with the operational parameters of the beam of optical energy. It is important in such procedures not to damage tissue underlying or surrounding the target tissue area. If the operational parameters of the beam of optical energy, such as wavelength, power, intensity of the optical energy, pulse duration, rate of emission, etc., are properly selected, cellular and interstitial water in the patient's skin is heated, causing temperature increases that produce a desired dermatological effect. Conversely, improper selection of the operational parameters can result in under-treatment or over-treatment of the tissue.

Dermatological treatments utilizing electromagnetic radiation often produce at least a low level of pain in the patient. Physicians typically use some method of reducing or relieving the pain experienced by the patient in order to make the patient more comfortable, such as, for example, oral analgesics and/or topical anesthetics prior to treatment. The methods of the present invention can be used to reduce or relieve the level of pain experienced by a patient during or immediately following a pain-inducing dermatological treatment. These methods can be used immediately before, during, or immediately following a dermatological treatment in order to reduce or relieve the level of pain produced in a patient by a pain-inducing dermatological treatment. These methods can be used continuously for a period of time immediately following a pain-inducing dermatological treatment in order to maintain the comfort of the patient following the treatment. Alternatively, these methods can be used intermittently for a long period of time following treatment on an as needed basis to maintain the comfort of the patient. These methods can be used alone in order to relieve pain, reduce pain and/or increase patient comfort. These methods can also be combined with other methods of providing analgesia and/or anesthesia in order to further decrease the level of pain experienced by a patient, or in order to decrease the concentration and/or dose of analgesia and/or anesthesia required.

The methods of the present invention reduce pain via non-pharmacologic means by stimulating a touch sensation in a tissue. The tissue can comprise a region of tissue that is to be treated using a dermatological treatment device. The tissue can comprise tissue near a region that is to be treated using a dermatological treatment device. The tissue can comprise tissue immediately adjacent to a region of tissue that is to be treated using a dermatological treatment device. The tissue can comprise a region of tissue which is larger than and encompasses the region of tissue that is to be treated using a dermatological treatment device.

The region of tissue to be treated by the pain-inducing dermatological treatment can comprise human tissue. The region of tissue to be treated by the dermatological treatment can comprise skin. The region of tissue to be treated by the dermatological treatment can comprise human skin. The region of tissue to be treated by the dermatological treatment can comprise one or more layers of human skin, such as, for example, the stratum corneum, the epidermis, the dermal-epidermal junction, the dermis, the subcutis, etc.

The touch sensation in the tissue is stimulated by directing multiple bursts of a gas at a tissue. The bursts of gas are of duration such as to stimulate a noticeable touch sensation in the region of tissue to which they are directed. The bursts of gas can comprise a series of bursts. The bursts and/or series of bursts of gas can be delivered in a pattern or in a random manner. The bursts and/or series of bursts can be delivered at a rate between about 5 bursts per second and about 100 bursts per second. The bursts and/or series of bursts can be delivered at a rate between about 7 bursts per second and about 50 bursts per second. The bursts and/or series of bursts can be delivered at a rate between about 10 bursts per second and about 30 bursts per second.

In one embodiment, the bursts of gas can comprise bursts of pressurized gas. The pressure of the bursts of gas can be between about 0.01 pound per square inch (psi) and about 10 psi. The pressure of the bursts of gas can be between 0.05 psi and about 5 psi. The pressure of the bursts of gas can be between about 0.1 psi and about 2 psi. In one embodiment, the gas can comprise air. Alternatively, the gas can comprise a substantially pure inert gas or mixture of inert gasses. The gas can comprise nitrogen.

In one embodiment, the temperature of the gas is approximately the ambient temperature in the treatment space at the time the gas contacts the tissue. For example, the average temperature of the gas can be between about 20° C. and about 30° C. at the time it contacts the tissue. Alternatively, the temperature of the gas can be significantly above or below the ambient temperature in the treatment space at the time the gas contacts the tissue in order to stimulate both a touch sensation and a temperature sensation in the tissue. For example, the average temperature of the gas can be above about 30° C., or below about 20° C. at the time it contacts the tissue.

In one embodiment, the pain-inducing dermatological treatment comprises an optical energy based treatment. The optical energy can be coherent in nature, such as laser radiation, or non-coherent in nature, such as flash lamp radiation. Coherent optical energy can be produced by lasers, including gas lasers, dye lasers, metal-vapor lasers, fiber lasers, diode lasers, and/or solid-state lasers. If a laser is used for the source of optical energy, the type of laser can be selected from the group consisting of an argon ion gas laser, a carbon dioxide (CO2) gas laser, an excimer chemical laser, a dye laser, a neodymium yttrium aluminum garnet (Nd:YAG) laser, an erbium yttrium aluminum garnet (Er:YAG) laser, a holmium yttrium aluminum garnet (Ho:YAG) laser, an alexandrite laser, an erbium doped glass laser, a neodymium doped glass laser, a thulium doped glass laser, an erbium-ytterbium co-doped glass laser, an erbium doped fiber laser, a neodymium doped fiber laser, a thulium doped fiber laser, an erbium-ytterbium co-doped fiber laser, and combinations thereof. The optical energy can be applied in a fractional manner to produce fractional treatment. For example, the FRAXEL® SR 1500 laser (Reliant Technologies, Inc. Mountain View, Calif., USA) produces fractional treatments using an erbium-doped fiber laser operating at a wavelength that is primarily absorbed by water in tissue, at about 1550 nm.

The wavelength of the optical energy used in the treatment can be between about 600 nm and about 20,000 nm. The wavelength of the optical energy can be selected based on the absorption strength of various components within the tissue and the scattering strength of the tissue. The wavelength of the optical energy can be chosen to target a particular chromophore, such as, for example, water, elastin, collagen, sebum, hemoglobin, myoglobin, melanin, keratin, or other endogenous or exogenous molecules present in the tissue. Wavelengths that are primarily absorbed by water present in the tissue, such as, for example, 1550 nm, can be used. The wavelength of the optical energy treatment can be within the near infrared spectrum, such as, for example, between about 700 nm and about 1400 nm. Wavelengths in the visible spectrum, such as, for example, between about 400 nm and about 700 nm are also useful. Ultraviolet optical energy within the range of between about 200 nm to about 400 nm can be used. These wavelengths can be particularly effective for allowing lower levels of radiation to be used to activate photodynamic therapeutic agents for treatment of conditions in the papillary and reticular dermis.

When the pain-inducing dermatological treatment comprises a fractional optical energy based treatment, depending on the desired size and depth of the treatment zones, the wavelength of the optical energy used can be selected from the group consisting of between about 1100 nm and about 2500 nm, between about 1280 nm and about 1350 nm, between about 1400 nm and about 1500 nm, between about 1500 nm and about 1620 nm, between about 1780 nm and 2000 nm, and combinations thereof. Wavelengths longer than 1500 nm and wavelengths with absorption coefficients in water of between about $1\ cm^{-1}$ and about $30\ cm^{-1}$ can be used if the goal is to get deep penetration with small treatment zones. The shorter wavelengths generally have higher scattering coefficients than the longer wavelengths.

In some examples, the optical energy can have a wavelength that is highly absorbed in water. Cellular water absorbs optical energy and transforms the optical energy into heat. Wavelengths larger than 190 nm, such as wavelengths in the range from 190 nm to 10600 nm, from 700 nm to 1600 nm, and about 1550 nm can used. The source of optical energy used to provide the treatment can be capable of providing one wavelength or a range of wavelengths or can be tunable across a range of wavelengths. One or more sources of optical energy can be used to produce a variety of different wavelengths or wavelength ranges used in the dermatological treatment. The optical energy source can be adapted to selectively produce pulses of optical energy at a frequency of between about 0 and about 50,000 pulses per second, or between about 0 and about 1,000 pulses per second. In one example, an optical energy source can emit a beam having pulse energy per treatment spot of between about 1 mJ and about 1000 mJ, or between about 10 mJ and about 30 mJ, with each pulse having a pulse duration per treatment spot between about 0.1 ms and about 30 ms, or about 1 ms.

In some embodiments, the pain-inducing dermatological treatment can be used, for example, to produce non-ablative coagulation of an epidermal and/or a dermal layer of tissue. Typically, for this purpose, an optical fluence incident to a tissue area greater than about 5 $J/cm^2$, such as an optical fluence in the range from about 10 $J/cm^2$ to about 1000 $J/cm^2$, is adequate for coagulating tissue. Generally, the optical fluence is adapted to the wavelength and the tissue to be treated. If various dermatological effects are desired, a treatment device can be selected with the capacity to produce source parameters suitable for other types of tissue treatment. For example, if ablation of an epidermal layer of the tissue is desired, a treatment device can be used with the capability to emit a beam of optical energy with a wavelength of about 2940 nm and optical fluence higher than about 10 $J/cm^2$.

Various methods of rating or scoring pain levels exist in the literature. For example, pain can be scored using a numerical analog score, a verbal assessment score, a verbal pain score, a visual analog score, etc. Such scoring systems are typically based on a continuum of possible scores or a series of possible scores where the lowest possible score is no pain, and the highest possible score is the worst pain imaginable. Other such scoring systems can be based on a scale representing low, medium, or high levels of pain.

One commonly used scoring system is a verbal pain assessment method where the patient is asked to verbally assign a score to their pain and/or discomfort at several points during the treatment. The score can be based on a 10 point scale, where 0 represents no pain and 10 represents the worst pain imaginable. In one example, when such a 10 point pain scale is used, a score of 8 or below can be considered to be a desirable level of pain for a patient to experience during or following a dermatological treatment. A reduction in an average pain score of one point on this scale can be considered to be a desirable and effective reduction in pain. For example, if for a patient a pain-reducing method results in a reduction in an average pain score of at least one point on this scale, the method can be considered to have been effective in reducing the patient's pain. If for a patient a pain-reducing method results in a reduction in an average pain score of at least two points on this scale, the method can be considered to have been more effective in reducing the patient's pain.

The methods of the present invention can be used alone or in combination with other methods of reducing or relieving pain. For example, these methods can be used in conjunction with oral analgesics, topical analgesics, topical anesthetics, injectable anesthetics, etc. The methods of the present invention can be used to reduce the dosage of an analgesic and/or anesthetic required to relieve and/or reduce the level of pain experienced by a patient undergoing a pain-inducing dermatological treatment.

A number of different types of topical anesthetics at various concentrations and dosages are commonly used to reduce or relieve the pain of dermatological treatments. For example, commonly used topical anesthetics include of lidocaine, prilocaine, tetracaine, benzocaine, dibucaine, oxybuprocaine, pramoxine, proparacaine, proxymetacaine, as well as combinations of topical anesthetics and other active ingredients. The non-pharmacologic methods of the present invention can be used to augment the effect of these active ingredients in order to relieve or reduce pain.

For example, the methods of the present invention can be used to reduce the concentration and/or dosage of an active ingredient that is required to produce a desired level of pain relief and/or reduction. If combining a pain-reducing method of the present invention with an active ingredient produces a reduction in an average pain score of at least one point on a ten point pain scale, the method can be considered to have been effective in relieving and/or reducing the patient's pain. If combining a pain-reducing method of the present invention with an active ingredient produces a reduction in an average pain score of at least two points on a ten point pain scale, the method can be considered to have been more effective in relieving and/or reducing the patient's pain. Alternatively, if combining a pain-reducing method of the present invention with an active ingredient can reduce the dosage and/or concentration of the active ingredient required by at least 10% in order to produce a similar average pain scale as compared to the use of the active ingredient alone, the method can be considered to have been effective in reducing the dosage and/or concentration of active ingredient required. If combining a pain-reducing method of the present invention with an active ingredient can reduce the dosage and/or concentration of the active ingredient required by at least 20% in order to produce a similar average pain scale as compared to the use of the active ingredient alone, the method can be considered to have been more effective in reducing the dosage and/or concentration of active ingredient required.

FIG. 1 is a drawing illustrating one example of a gas burst production system 130 that can be used to stimulate a touch sensation in tissue 150 by directing multiple bursts of a gas at a region of tissue so as to reduce and/or relieve pain produced by a dermatological treatment. In FIG. 1, the gas source 160 can comprise a system that produces a stream of gas 132, such as, for example, an air compressor, an air blower, a source of pressurized gas, etc.

The stream of gas 132 is directed out of the gas source 160 and toward a burst production system 170. The burst production system serves to divide the stream of gas 132 into individual bursts of gas 133. The burst production system can comprise, for example, a rotating fan, a rotating wheel with alternating open and closed apertures, etc. The burst production system can divide the stream of gas into a series of bursts. The burst production system can divide the stream of gas into a pattern of bursts with a set frequency and/or delay. The burst production system can divide the stream of gas into a random series of burst without a set frequency and/or delay. The timing of the bursts is such that, when the bursts are directed at a tissue, the bursts produce a touch sensation in the tissue 150. Once the bursts of gas 133 leave the gas burst production system 130, they are directed to the tissue 150 by a gas burst delivery system 131. The gas burst delivery system 131 can comprise, for example, a tube or other such housing.

The gas burst production system of FIG. 1 can be used as a separate device in order to stimulate a touch sensation in a tissue. Alternatively, the gas burst production system of FIG. 1 can be incorporated into a dermatological treatment device in order to more easily deliver the multiple bursts of gas immediately before, during or immediately following a dermatological treatment.

Figure 2:
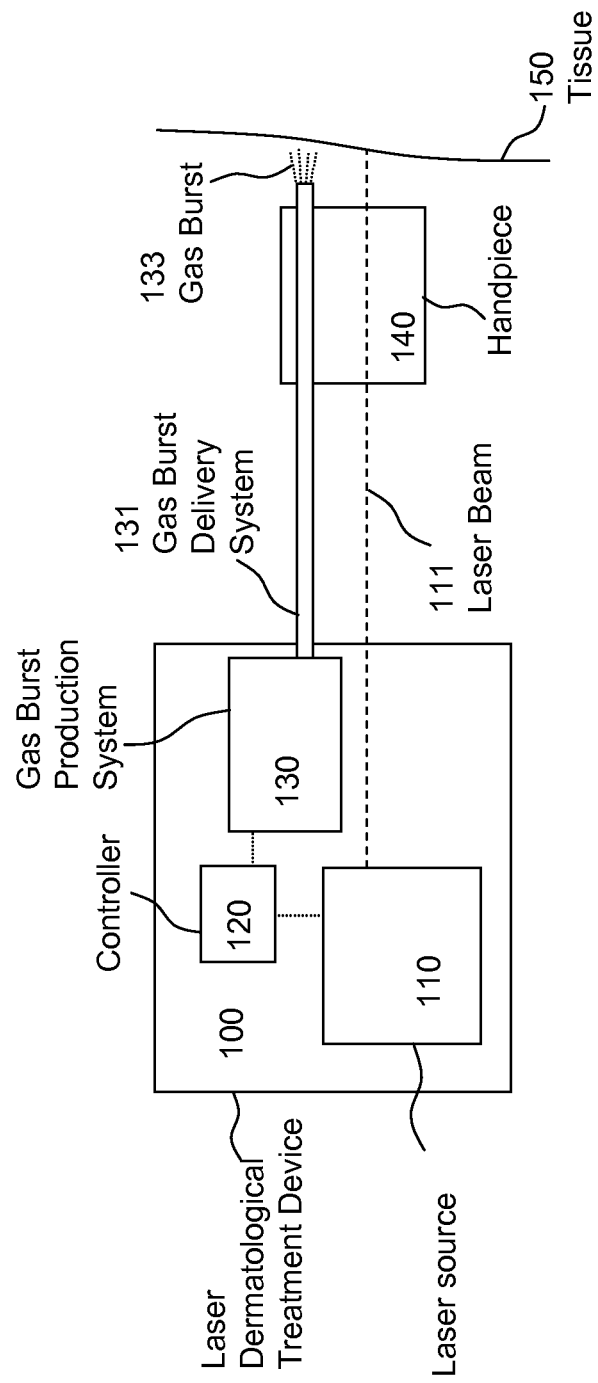
FIG. 2 is a drawing illustrating an electromagnetic energy based medical treatment system which incorporates a gas burst production system being used to deliver busts of gas during an electromagnetic energy based treatment to a tissue.

FIG. 2 illustrates a laser dermatological treatment which incorporates a gas burst production system such as, for example, the gas burst production system of FIG. 1. The treatment device of FIG. 2 comprises a laser source 110, a gas burst production system 130, a controller, a gas burst delivery system 131, and a handpiece 140. In the device of FIG. 2, the laser source 110 and the gas burst production system 130 are controlled by the controller 120. Optionally, other components of the device, such as the handpiece, can be controlled by the controller as well. In the device of FIG. 2, the gas burst production system 130 produces multiple bursts of gas which are directed by the gas burst delivery system 131 through the handpiece 140 to a tissue 150, where the multiple gas bursts stimulate a touch sense in the tissue. The gas bursts 133 can be directed at the tissue immediately before, during, and immediately following the laser treatment.

EXAMPLES

Example 1

Reduction of Pain During Laser Skin Resurfacing

Five patients are recruited to participate in a study to evaluate the level of pain reduction produced by the use of a gas burst production system in conjunction with a fractional laser skin resurfacing treatment. The study parameters and requirements are fully explained to each patient, and each patient signs a consent form prior to start of the study.

On the day of the treatment, each patient is prepared for the treatment by applying a thick layer (about ¼ inch) of a commercially available topical anesthetic cream, such as EMLA® Cream lidocaine and prilocaine cream (AstraZeneca, Wilmington, Del., USA) to the entire face. The cream is left in place for approximately 45 minutes. Immediately prior to treatment, the cream is removed from the patient's face.

Each patient receives a skin resurfacing treatment on their face using a FRAXEL® SR 1500 laser (Reliant Technologies, Inc. Mountain View, Calif., USA) at settings appropriate for their skin type. On half the face of each patient, multiple bursts of gas are directed at the skin in a manner which produces a touch sensation. The multiple bursts of gas are delivered to the skin essentially concurrently with the laser treatment. The multiple bursts of gas are produced using a Zimmer Cryo 6 cold air device (Zimmer MedizinSystems, Irvine, Calif., USA) which has been modified to include a rotating wheel with apertures which breaks the stream of cold air into bursts, producing a series of bursts of cold air at a rate of approximately 10 bursts per second. On the other half of the face of each patient, a steady stream of gas is directed at the skin essentially concurrently with the laser treatment. The steady stream of gas is provided using the same Zimmer Cryo 6 cold air device at the same settings as previously, but with the rotating wheel with apertures removed in order to allow the device to deliver the cold air in a stream rather than bursts.

During the treatment, the patients are verbally asked to assess their pain level using a 10 point pain scale, where zero is the absence of pain and 10 is the worst pain imaginable. At least 5 pain scores are recorded for each half of the face treated for each patient, and are averaged to obtain an average pain score for each treatment type (with a steady stream of cold air or with multiple bursts of cold air) for each patient. The two average pain scores for each patient are then compared, and the average pain scores for the treatments using multiple bursts of cold air are found to be at least one point lower than the average scores for the treatments using a stream of cold air.

All publications, patents and patent applications cited herein, whether supra or infra, are hereby incorporated by reference in their entirety.

In the specification and in the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

What is claimed is:

1. A method of reducing the level of pain experienced by a patient during a pain-inducing dermatological treatment, comprising:
   stimulating a touch sensation in a patient in an area in or near a region of tissue to be treated during a pain-inducing dermatological treatment,
   wherein the stimulating of the touch sensation is achieved by directing multiple bursts of a gas at or near the region of tissue so as to reduce the level of pain experienced by the patient during the pain-inducing dermatological treatment.

2. The method of claim 1, further comprising:
   providing the pain-inducing dermatological treatment to a patient.

3. A method of reducing the dosage of anesthetic required by a patient undergoing a pain-inducing dermatological treatment, comprising:
   stimulating a touch sensation in a patient in an area in or near a region of tissue to be treated during a pain-inducing dermatological treatment,
   wherein the stimulating of the touch sensation is achieved by directing multiple bursts of a gas at or near the region of tissue, and
   wherein the stimulating of the touch sensation reduces the dosage of anesthetic required to reduce the level of pain experienced by a patient undergoing the pain-inducing dermatological treatment.

4. The method of claim 3, wherein the method comprises stimulating a touch sensation in the region of tissue to be treated by the pain-inducing dermatological treatment.

5. The method of claim 3, wherein the method comprises stimulating a touch sensation in a region of tissue immediately adjacent to the region of tissue to be treated by the pain-inducing dermatological treatment.

6. The method of claim 3, wherein the method comprises stimulating a touch sensation in a region of tissue which is larger than and encompasses the region of tissue to be treated by the pain-inducing dermatological treatment.

7. The method of claim 3, wherein the region of tissue to be treated comprises human skin.

8. The method of claim 3, wherein the multiple bursts of gas are delivered at a rate between about 5 bursts per second and about 100 bursts per second.

9. The method of claim 3, wherein the multiple bursts of gas are delivered at a rate between about 5 bursts per second and about 50 bursts per second.

10. The method of claim 3, wherein the multiple bursts of gas are delivered at a rate between about 10 bursts per second and about 30 bursts per second.

11. The method of claim 3, wherein the multiple bursts of gas comprise bursts of pressurized gas.

12. The method of claim 3, wherein the gas comprises air.

13. The method of claim 1 or 3, wherein the gas comprises nitrogen.

14. The method of claim 3, wherein the temperature of the gas is approximately ambient temperature as it contacts the tissue.

15. The method of claim 3, wherein the temperature of the gas is between about 20° C. and about 30° C. as it contacts the tissue.

16. The method of claim 3, wherein the temperature of the gas is below about 20° C. as it contacts the tissue.

17. The method of claim 3, wherein the temperature of the gas is above about 30° C. as it contacts the tissue.

18. The method of claim 3, wherein the pain-inducing dermatological treatment comprises an optical energy based treatment.

19. The method of claim 3, wherein the pain-inducing dermatological treatment comprises a laser treatment.

20. The method of claim 3, wherein the average pain score experienced by a patient undergoing the pain-inducing dermatological treatment in conjunction with the stimulating is at least 1 point less on a 10 point pain scale than the average pain score experienced by a patient undergoing the pain-inducing dermatological treatment in the absence of the stimulating, where a score of zero is no pain and a score of 10 is the worst pain imaginable.

21. The method of claim 20, wherein the topical anesthetic is selected from the group consisting of lidocaine, prilocaine, tetracaine, benzocaine, dibucaine, oxybuprocaine, pramoxine, proparacaine, proxymetacaine, and combinations thereof.

22. The method of claim 3, wherein the average pain score experienced by a patient undergoing the pain-inducing dermatological treatment in conjunction with the stimulating is at least 2 points less on a 10 point pain scale than the average pain score experienced by a patient undergoing the pain-inducing dermatological treatment in the absence of the stimulating, where a score of zero is no pain and a score of 10 is the worst pain imaginable.

23. The method of claim 3, wherein the anesthetic comprises a topical anesthetic.

24. The method of claim 3, wherein the dosage of anesthetic required to reduce the level of pain experienced by a patient undergoing the pain-inducing dermatological treatment in conjunction with the stimulating is at least 20% less than the dosage of anesthetic required to reduce the level of pain experienced by a patient undergoing the pain-inducing dermatological treatment in the absence of the stimulating.

25. The method of claim 24, wherein a dosage of anesthetic required to reduce the level of pain experienced by a patient undergoing the pain-inducing dermatological treatment in the absence of the stimulating comprises the dosage of anesthetic required to prevent the patient from experiencing pain in excess of a pain score of 8 on a 10 point pain scale, where a score of zero is no pain and a score of 10 is the worst pain imaginable.

26. The method of claim 3, further comprising:
   providing the pain-inducing dermatological treatment to a patient.

* * * * *